United States Patent [19]

Warriner

[11] Plant 5,249

[45] Jun. 26, 1984

[54] ROSE PLANT—JACFUN

[75] Inventor: William A. Warriner, Tustin, Calif.

[73] Assignee: Jackson & Perkins Co., Medford, Oreg.

[21] Appl. No.: 422,484

[22] Filed: Sep. 23, 1982

[51] Int. Cl.[3] ..... A01H 5/00

[52] U.S. Cl. ..... Plt./9

[58] Field of Search ..... Plt./9

*Primary Examiner*—Robert E. Bagwill

*Attorney, Agent, or Firm*—Klarquist, Sparkman, Campbell, Leigh & Whinston

[57] ABSTRACT

A miniature rose variety having compact plant habit which blooms at two feet or less, petals with pink upper sides and deeper pink lower sides, large prickles, good mildew resistance, and mild fragrance.

1 Drawing Figure

This present invention relates to a new and distinct variety of rose plant of the miniature class which was originated by me by crossing the variety Bridal Pink, U.S. Plant Pat. No. 2,851, with the variety Fire Princess, U.S. Plant Pat. No. 3,084.

The primary objective of this breeding was to produce a new rose variety combining the flower color and form of Bridal Pink with the miniature growth habit of Fire Princess. This objective was substantially achieved along with other desirable improvements as evidenced by the following unique combination of characteristics which are outstanding in the new variety and which distinguish it from its parents, as well as from all other varieties of which I am aware:

1. Plant habit is very compact, reaching approximately three feet maximum, normally blooming at two feet or less.
2. Flower color is pink (RHS 55D) on upper side of petals, deeper pink (RHS 48D) on lower side.
3. Large, straight, brown prickles.
4. Good resistance to mildew.
5. Mild fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Bridal Pink, U.S. Plant Pat. No. 2,851.

*Pollen parent.*—Fire Princess, U.S. Plant Pat. No. 3,084.

Classification:

*Botanical.*—Rosa hybrid.

*Commercial.*—Miniature.

FLOWER

Observations made from specimens grown at Irvine, Calif. in July, 1982.

Blooming habit: Continuous.

Bud:

*Size.*—$\frac{5}{8}''$ to $\frac{3}{4}''$ when petals start to unfurl.

*Form.*—Pointed ovoid.

*Color.*—When sepals first divide, Red Group 48A. When half blown; upper side of petals Red Group 49D, lower side of petals Red Group 48A.

*Sepals.*—Color: Outer surface Green 138A overlaid with Greyed Purple 184A, and containing numerous stipitate glands. Three appendaged sepals lightly appendaged. Two unappendaged sepals hairy edged.

*Receptacle.*—Color: Green 138A, occasionally overlaid with Greyed Purple 184A. Shape: Pear. Size: Large. Surface: Slightly hairy.

*Peduncle.*—Length: Short. Surface: Glandular. Color: Light green and bronzy. Strength: Stiff, erect.

*Opening.*—Spiral type.

Bloom:

*Size.*—Small. Average open size is $1\frac{3}{4}''$ to $2''$.

*Borne.*—In clusters, flat.

*Stems.*—Short, strong.

*Form.*—When first open, flat. Permanence: Retains its form to the end; outer petal edges slightly curled.

*Petalage.*—Number of petals under normal conditions: 30–35.

*Color.*—Center of flower: Upper side of petals Red Group 55D; reverse side of petals Red Group 48D; base of petals near white. General tonality from a distance Pink (Red Group 55D).

*Variegations.*—None.

*Discoloration.*—General tonality at end of first day: No change. Third day: Much lighter than Red Group 55D.

*Fragrance.*—Slight, zinnia-like.

Petals:

*Texture.*—Leathery.

*Shape.*—Obovate.

*Form.*—Edges slightly quilled.

*Arrangement.*—Roughly imbricated. Petaloids in center, few.

*Persistence.*—Drop off cleanly.

*Lastingness.*—On the plant, long. As cut flower, long.

Reproductive parts:

*Anthers.*—Large. Color: Golden yellow. Arrangement: Regular around styles.

*Filaments.*—Color: White.

*Pollen.*—Gold yellow.

*Styles.*—Color: Reddish.

*Stigmas.*—Color: White.

PLANT

Form: Bush.

Growth: Vigorous, branching, compact, growing to under 3'.

Foliage: Number of leaflets on normal mid-stem leaves: 5–7.

*Size.*—Medium.

*Quantity.*—Abundant.

*Color.*—New foliage: Green 138A, overlaid heavily with Greyed Purple 187C. Old foliage: Green 137A.

Leaflets:

*Shape.*—Elliptic.

*Texture.*—Upper side: Leathery.

*Edge.*—Serrated.

*Serration.*—Single, small.

*Petiole.*—Rachis: Color: Green. Underside: Large prickles.

*Stipules.*—Long, bearded.

*Disease resistance.*—Resistance to mildew, blackspot under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, many. On laterals from stalk, many.

*Form.*—Long, straight.

*Color when young.*—Brown.

*Position.*—Irregular.

Small Prickles:

*Quantity.*—On main stalks, few. On laterals, few.

*Color.*—Brown.

I claim:

1. A new and distinct variety of rose plant of the miniature class, substantially as herein shown and described, characterized particularly as to novelty by the unique combination of its miniature plant habit, pink flowers with darker reverse side, large prickles and mild fragrance.

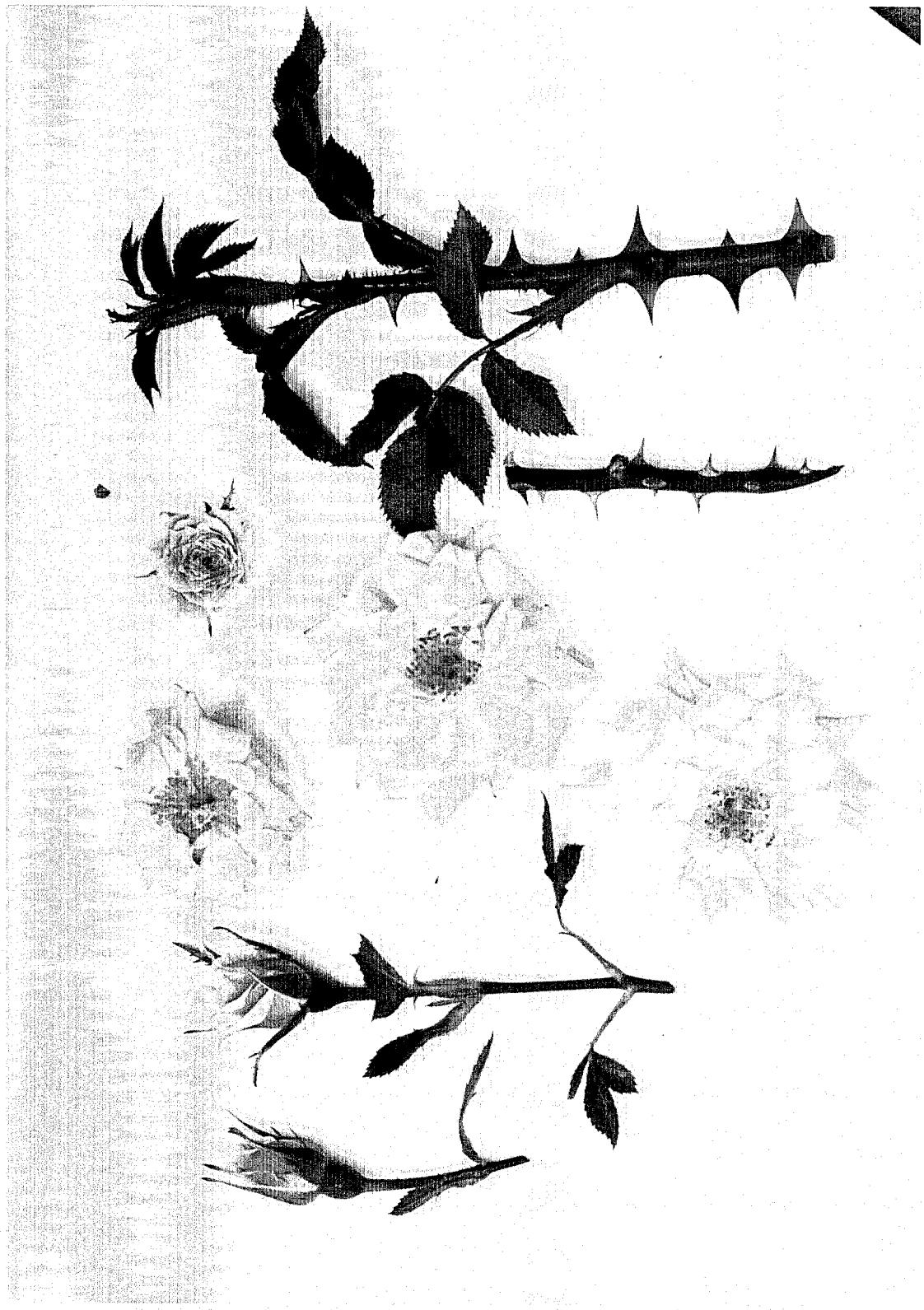

* * * * *